United States Patent [19]

Maunders

[11] Patent Number: 5,723,713
[45] Date of Patent: Mar. 3, 1998

[54] ETHYLENE CONVERSION PROCESS

[75] Inventor: Barry Martin Maunders, Martigues, France

[73] Assignee: BP International Limited, London, England

[21] Appl. No.: 693,020

[22] Filed: Aug. 6, 1996

[30] Foreign Application Priority Data

Dec. 6, 1994 [GB] United Kingdom .............. 942457

[51] Int. Cl.$^6$ .................. C07C 2/10; C07C 2/00
[52] U.S. Cl. ............. 585/533; 585/502; 585/510; 585/520; 585/530; 585/531; 585/532; 585/329
[58] Field of Search ................... 585/502, 510, 585/520, 530, 531, 532, 533, 329

[56] References Cited

U.S. PATENT DOCUMENTS

| | | | |
|---|---|---|---|
| 3,341,620 | 9/1967 | Clark et al. | 260/683.15 R |
| 3,647,906 | 3/1972 | Farley | 260/683 D |
| 3,658,927 | 4/1972 | Crain et al. | 260/666 A |
| 3,689,589 | 9/1972 | Reusser | 260/683.15 R |
| 4,665,245 | 5/1987 | Quann | 585/316 |
| 4,795,734 | 1/1989 | Chauvin et al. | 502/355 |
| 5,055,628 | 10/1991 | Lin et al. | 585/647 |
| 5,057,644 | 10/1991 | Lin et al. | 585/850 |
| 5,134,241 | 7/1992 | Le et al. | 585/332 |
| 5,162,595 | 11/1992 | Wu | 585/510 |
| 5,162,597 | 11/1992 | Wu | 585/646 |
| 5,180,863 | 1/1993 | Forbus | 585/7 |

FOREIGN PATENT DOCUMENTS

| | | |
|---|---|---|
| 0 232 617 B1 | 8/1987 | European Pat. Off. . |
| 0 276 096 | 7/1988 | European Pat. Off. . |

*Primary Examiner*—Helane Myers
*Assistant Examiner*—Nadine Preisch
*Attorney, Agent, or Firm*—Nixon & Vanderhye

[57] ABSTRACT

This invention relates to a process for the converting ethylene to a mixture of 1-olefins by (a) feeding ethylene through an oligomerization catalyst bed to form an oligomer predominating in C2-C6 olefins and (b) feeding the oligomer, optionally admixed with fresh ethylene, containing at least 50% by volume ethylene, through a metathesis catalyst bed to form a product predominating in C2-C6 1-olefins. Steps (a) and (b) can be carried out sequentially and in a single reactor under the same conditions of reaction temperature and pressure. This mitigates the perceived disadvantages of low activity and low conversions of relatively inexpensive oligomerization catalysts and forms oligomer having the desired distribution of 1-olefin components for use as comonomer in a polyolefin process.

16 Claims, No Drawings

ETHYLENE CONVERSION PROCESS

The present invention relates to a process for the conversion of ethylene to a mixture of lower olefins by subjecting ethylene to a sequential oligomerisation and metathesis using a separate catalyst system for each stage in order to produce a mixture of products which is suitable for use as a comonomer during the polymerisation of olefins.

It is well known to use comonomers such as eg butene-1 or hexene-1 during the production of some grades of polyethylene such as linear low density polyethylene (hereafter "LLDPE"). However, the cost of eg hexene-1 comonomer is significantly more than the cost of ethylene primarily because the comonomer is produced by a dedicated process. Thus, the potential for improving the economics of the process by producing the comonomers cheaply is significant. Hitherto, such comonomers have been synthesised on the polyethylene plant for instance by passing part or all of the ethylene feed over an oligomerization catalyst to selectively produce 1-olefins in situ. The oligomerization process is usually operated to maximise the yield of the oligomer and hence relatively higher reaction temperatures and pressures as well as stronger and relatively expensive oligomerization catalysts are used. Such catalysts are highly reactive and are therefore air sensitive and deactivate readily. Also, such an oligomerization process produces a mixture of linear olefins but the distributions of the various oligomeric 1-olefins in the mixture is not always constant. Moreover, the amount of non-polymerizable components (such as eg butene-2) of such a mixture is significantly above the preferred maximum tolerance level of 1 to 1.5 mole % and therefore cannot be fed directly to the ethylene polymerization process without further purification to minimise the concentration of the non-polymerizable components therein. In addition, the reaction pressure and temperature used for the oligomerization process to obtain the right proportion of components in the mixture of oligomers is often at variance with the process used for producing polyethylene from ethylene, especially in the conventional gas phase process. Furthermore, the oligomerization products thus produced is a complex mixture which has to be separated/purified in order to ensure that the higher 1-olefins therein are not fed to the polymerization stage. Such higher olefins are usually separated and sold to the detergent alkylate industry.

It has now been found that such conversion of ethylene to the desirable mixture of lower olefins can be increased above 10% and up to 30% by subjecting ethylene to a combined oligomerization and metathesis process.

Accordingly, the present invention is a process for the conversion of ethylene to a mixture of olefins predominating in 1-olefins said process comprising a. feeding ethylene through a bed of an oligomerization catalyst to form an oligomer predominating in C2–C6 olefins and b. feeding the oligomer so formed either as such or after admixture thereof with further aliquots of ethylene so as to maintain the concentration of ethylene in the oligomer to at least 50% by volume through a catalyst bed to metathesise the oligomer feed to a mixture of olefinic products predominating in C2–C6 1-olefins.

The oligomerization catalyst used in step (a) suitably comprises at least one metal or at least one oxide of a metal selected from Groups VIA, VIIA and VIIIA according to the Periodic Table (IUPAC) deposited or impregnated on a support either as such or by ion-exchange with a solution of the metal salt which may for example be a nitrate, acetate or oxalate, followed by calcination. The catalyst suitably has 0.1–50% w/w of the metal as such or in the form of its oxide, preferably from 1 to 20% w/w. The aluminosilicate support in the catalyst suitably has a silica to alumina ratio of 20:1 to 500:1, preferably from about 60:1 to 200:1. More specifically, the oligomerization catalyst used is preferably such that under the reaction conditions, the conversion of ethylene to the oligomer is suitably below 30% at steady state. An example of such a metal oxide is nickel oxide and an example of a suitable support is an aluminosilicate such as eg grade SP 2-8341 (ex Grace GmbH). The oligomerization catalyst is suitably activated prior to use. The activation is suitably carried out by calcining initially in air and then optionally in an inert atmosphere, eg nitrogen, at an elevated temperature, eg about 500° C. The same process can be used to regenerate the used catalyst.

The oligomerization reaction (a) is suitably carried out at pressures ranging from 100 to 10000 kPa, preferably 500–5000 kPa, and at a temperature ranging from ambient to 120° C. in order to obtain an oligomer which predominates in C2–C6 olefins. In such a process, at relatively lower temperatures within this range, the conversion of ethylene is suitably maintained below 30% at steady state and the oligomer is rich in 1-olefins and hence the subsequent metathesis of such an oligomer results in a product mixture which is rich in ethylene. At relatively higher temperatures, the oligomer comprises a significant proportion of 2-olefins such as butene-2; metathesis of such an oligomer gives rise to a product mixture rich in propylene.

The oligomer feed to the metathesis step (b) is suitably such that said feed is rich in ethylene in order to achieve the desired metathesis. The concentration of ethylene in this oligomer feed should be at least 50% v/v, suitably at least 70% v/v and preferably at or above 80% v/v. Using an olefinic feed to the metathesis step rich in ethylene ensures that self-metathesis amongst the higher olefin components of such a feed is minimised and the product mixture emergent from the metathesis step has the desired distribution of 1-olefins therein. The desired concentration of ethylene in the feed to the metathesis step (b) to at least 50% v/v can be achieved either i. by controlling the oligomerization reaction conditions in step (a) to achieve a low conversion of ethylene or ii. by carrying out step (a) to achieve a higher conversion of ethylene to the oligomers but admixing the oligomerization product with further aliquots of fresh ethylene in order to bring the concentration thereof in the feed to the metathesis step (b) to at least 50% v/v.

The metathesis reaction (b) of the oligomer from step (a) is suitably carried out using a metathesis catalyst comprising at least one metal or at least one oxide of a metal from Group VIA or Group VIIA of the Periodic Table (IUPAC). The metathesis catalyst is preferably used in the heterogeneous phase. If the catalyst is used in a heterogeneous phase, it is suitably in the form of a metal oxide deposited or impregnated on a support. The amount of metal oxide on the support in the metathesis catalyst is suitably in the range from 0.1 to 15% w/w, preferably 0.5–12% w/w based on the total weight of the metal oxide and the support. Examples of suitable metal oxides include oxides of rhenium, tungsten, cobalt or molybdenum. Examples of suitable supports which may be used include alumina, phosphated alumina, silica and aluminosilicates. Rhenium heptoxide on alumina is preferred. The metathesis catalyst is suitably a heterogeneous catalyst and is activated prior to use. The activation is suitably carried out by calcining initially in air and then optionally in an inert atmosphere, eg nitrogen, at an elevated temperature, eg about 500° C. The same process can be used to regenerate the used catalyst. A feature of the present invention is that the oligomerization and metathesis can be carried out under the same conditions of reaction temperature and pressure. Thus, by using a combined oligomerization and metathesis process carried out sequentially and in a single reactor, the perceived disadvantages of relatively inexpensive oligomerization catalysts such as low activity and low conversions can be mitigated to obtain the desired oligomer having the desired distribution of 1-olefin components therein thereby improving the economics of the polyolefin process.

The present invention is further illustrated with reference to the following Examples:

A. Catalyst Preparation:

A1. Nickel oxide aluminosilicate:

Nickel nitrate hexahydrate (5.71 g) was dissolved in de-ionised water (79.83 g) and aluminosilicate particles (29.75 g, 70μparticle size, Grade SP 2-8341 ex Grace GmbH) added to form a gel. The gel was dried (100° C.) and calcined (500° C.) in flowing air (2 liters per minute) in a muffle furnace. The nickel oxide impregnated catalyst so formed was then pressed at 16 tonnes, broken up and sieved. Particles of 0.5–1.0 mm were used as the catalyst for the oligomerization reactions. The amount of nickel nitrate used was sufficient to give a nickel oxide loading of 3.84% w/w.

A2. Rhenium heptoxide on alumina:

The rhenium heptoxide-alumina catalyst (Q195-01, ex Engelhard Industries) was an experimental sample supplied as extrudates. These were broken up into particles of 0.5–1.0 mm and were used in the catalytic metathesis reactions. The metal oxide loading was 3.9% w/w as rhenium heptoxide.

B. Reactions:

B1. Oligomerization:

Two separate runs C1 and C2 were performed with the catalyst prepared in A1 above.

B1.1. Run C1:

Run C1 used catalyst A1 (4 g=16 ml) activated in nitrogen (100 ml/minute) at 300° C., atmospheric pressure for 3 hours and then cooled to ambient temperature.

The reactor for run C1 was pressurised in nitrogen (2500 KPa). The nitrogen flow was switched to ethylene (WHSV 7.5/hr) at ambient temperature. An exotherm of about 50° C. was observed and initial conversion peaked at around 40–50% before fairly quickly decaying. The temperature and ethylene flow rates were varied to try to maintain conversion. The results are shown in Table 1 below.

B1.2. Run C2:

Run C2 used catalyst A1 (1 g=3.8 ml) which was diluted by mixing with silicon carbide (carborundum) chips to give a total bed volume of 16 ml ie the same as for Run C1 above except that the WHSV was 6.4/hr. It was then activated as previously in Run C1 in nitrogen.

The oligomerization reaction was carried out in the same manner as in Run C1 above except that ethylene flow was introduced in two stages, with nitrogen backed-out to maintain a constant flow rate. With this procedure and catalyst dilution no exotherm was observed and the initial conversion was kept to 10%. Over 24 hours, the conversion fell to 2%. The temperature and ethylene flow rates were varied to try to maintain conversion as shown in Table 2.

B1.2.1. Catalyst Regeneration and Use:

After about 100 hours on stream (HOS), the catalyst was regenerated, the reactor was cooled to ambient temperature in flowing nitrogen and depressurised to atmospheric pressure. Air was introduced (10 ml/minute) and the reactor heated (at the rate of 3° C./hour) to 500° C. and maintained at this temperature for 10 hours. It was then cooled to 300° C. and purged with nitrogen (100 ml/minute) for 3 hours before cooling to ambient temperature.

The reactor was then pressurised again in nitrogen (2500 KPa) and the flow set to give a WHSV of 6.4/hour, based on the 1 g of nickel oxide aluminosilicate, at ambient temperature. Ethylene flow was then introduced in two stages, with nitrogen backed-out to maintain constant flow rate.

Compared to the first cycle of Run C1, the catalyst after regeneration was considerably more active. Ethylene conversion rose to almost 100% with, for the first time, significant quantities of liquid oligomers formed (see Table 2).

B1.2.2 Second Regeneration of Catalyst and Use:

A second regeneration of the catalyst was performed in a manner identical to that described in B1.2.1 above after 120 HOS. The same start-up procedure was used as previously and resulted in high ethylene conversion again, but this time with no liquid oligomer formation (see Table 2) below.

B2. Oligomerization/Metathesis:

Nickel oxide aluminosilicate catalyst (1 g=3.6 ml) made as in A1 above was diluted with carborundum chips to give a volume of 8 ml and then loaded in the top half of a reactor. Rhenium heptoxide alumina catalyst (2.5 g=4 ml) made as in A2 above was diluted with carborundum chips to give a volume of 8 ml and loaded in the bottom half of the same reactor.

An air flow (100 ml/minute) was established and the reactor heated (at the rate of 3° C./hour) to 500° C. and maintained at this temperature for 10 hours. It was then cooled to 300° C. and purged with nitrogen (100 ml/minute) for 3 hours before cooling to ambient temperature.

The reactor was then pressurised in nitrogen (2500 KPa) and the flow set to give a WHSV of 6.4/hour based on the 1 g of nickel oxide aluminosilicate catalyst at ambient temperature. Ethylene flow was then introduced in two stages, with nitrogen backed-out to maintain constant flow rate.

Initially, ethylene conversion rose to nearly 100% with a small amount of liquid products being observed in addition to gaseous products. The appearance of significant quantities of propylene and pentenes indicated that the metathesis catalyst was also active (see Table 3 below). At these high total ethylene conversion levels, significant butene self-metathesis reactions may occur.

As the ethylene conversion decayed, the selectivity to butenes increased, with high selectivity to butene-1; 7 to 16% total ethylene conversion, 72 to 76% selectivity to butenes with 97–98% of it butene-1. The other products were mainly propylene (about 15%), pentenes (4–7%-≧80% pentene-1) and hexenes (3–6%) (see Table 3).

TABLE 1

ETHYLENE OLIGOMERIZATION

| RUN REF | APPLIED TEMP (°C.) | CATALYST AV BED TEMP | ETHYLENE WHSV | HOS | ETHYLENE CONV (C mol %) | % SELECTIVITY TO C4's | | | % SELECTIVITY | | |
|---|---|---|---|---|---|---|---|---|---|---|---|
| | | | | | | 1-C4= | t-C4=2 | c-C4=2 | C4's | C6's | C8's |
| C1/1 | 21 | 47.6 | 7.5 | 0.1 | 49 | 18 | 54 | 28 | 100 | 0 | 0 |
| C1/2 | 21 | 53.6 | 7.5 | 0.7 | 24 | 46 | 31 | 23 | 87 | 10 | 3 |
| C1/3 | 21 | 40.3 | 7.5 | 1.4 | 15 | 66 | 18 | 16 | 94 | 5 | 1 |
| C1/4 | 21 | 38.3 | 7.5 | 1.9 | 13 | 70 | 16 | 14 | 95 | 5 | 0 |
| C1/5 | 21 | 36.6 | 7.5 | 2.4 | 11 | 75 | 13 | 12 | 91 | 7 | 2 |
| C1/6 | 21 | 34.6 | 7.5 | 3.1 | 10 | 78 | 11 | 11 | 90 | 9 | 1 |
| C1/7 | 21 | 33 | 7.5 | 3.9 | 7 | 83 | 9 | 8 | 85 | 13 | 2 |
| C1/8 | 21 | 31.6 | 7.5 | 4.6 | 7 | 85 | 8 | 7 | 83 | 16 | 1 |
| C1/9 | 21 | 30.3 | 7.5 | 5.4 | 6 | 86 | 7 | 7 | 81 | 18 | 1 |
| C1/10 | 21 | 22.6 | 7.5 | 23.3 | 1 | 95 | 2 | 3 | 97 | 3 | 0 |
| C1/11 | 60 | 109 | 7.5 | 24.2 | 9 | 38 | 34 | 28 | 97 | 2 | 1 |
| C1/12 | 60 | 97.3 | 7.5 | 24.5 | 11 | 41 | 30 | 29 | 98 | 2 | 0 |
| C1/13 | 60 | 73.3 | 7.5 | 25.1 | 5 | 69 | 14 | 17 | 78 | 22 | 0 |
| C1/14 | 60 | 63.3 | 7.5 | 25.4 | 3 | 76 | 11 | 13 | 75 | 23 | 2 |
| C1/15 | 60 | 61.6 | 7.5 | 26.1 | 2 | 77 | 11 | 12 | 83 | 9 | 8 |
| C1/16 | 60 | 61.6 | 7.5 | 26.7 | 2 | 85 | 7 | 8 | 87 | 5 | 8 |
| C1/17 | 60 | 61.6 | 7.5 | 27.1 | 2 | 86 | 7 | 7 | 90 | 7 | 3 |
| C1/18 | 60 | 61.6 | 3.3 | 29 | 3 | 89 | 5 | 6 | 86 | 8 | 6 |
| C1/19 | 60 | 61.3 | 3.3 | 45 | 0 | 100 | 0 | 0 | 100 | 0 | 0 |
| C1/20 | 120 | 133 | 3.3 | 48 | 36 | 34 | 34 | 32 | 90 | 10 | 0 |
| C1/21 | 120 | 128.6 | 3.3 | 50 | 24 | 44 | 26 | 30 | 89 | 10 | 1 |
| C1/22 | 120 | 126.3 | 3.3 | 52 | 19 | 48 | 24 | 28 | 89 | 10 | 1 |
| C1/23 | 120 | 125.6 | 3.3 | 69 | 22 | 47 | 24 | 29 | 91 | 8 | 1 |

TABLE 2

ETHYLENE OLIGOMERIZATION

| RUN REF | APPLIED TEMP (°C.) | CATALYST AV BED TEMP | ETHYLENE WHSV | HOS | ETHYLENE CONV (C mol %) | % SELECTIVITY TO C4's | | | % SELECTIVITY | | |
|---|---|---|---|---|---|---|---|---|---|---|---|
| | | | | | | 1-C4= | t-C4=2 | c-C4=2 | C4's | C6's | C8's |
| C2/1 | 20 | 20.6 | 6.3 | 1 | 10.2 | 83 | 9 | 8 | 98.3 | 1.4 | 0.3 |
| C2/2 | 20 | 21.3 | 6.3 | 3 | 4.8 | 92 | 4 | 4 | 95.9 | 4.1 | 0.0 |
| C2/3 | 20 | 21.3 | 6.3 | 6 | 4.0 | 93 | 4 | 4 | 96.9 | 3.1 | 0.0 |
| C2/4 | 20 | 28.6 | 6.4 | 24.5 | 3.0 | 93 | 3 | 4 | 97.2 | 2.8 | 0.0 |
| C2/5 | 20 | 25.6 | 6.4 | 25.5 | 2.6 | 94 | 3 | 3 | 95.9 | 4.1 | 0.0 |
| C2/6 | 20 | 23.6 | 6.4 | 26.5 | 2.1 | 95 | 3 | 3 | 97.6 | 2.4 | 0.0 |
| C2/7 | 60 | 61.6 | 6.4 | 28 | 7.7 | 84 | 8 | 9 | 97.3 | 2.7 | 0.0 |
| C2/8 | 60 | 61.6 | 6.4 | 29 | 5.8 | 86 | 7 | 8 | 94.5 | 5.5 | 0.0 |
| C2/9 | 60 | 61.6 | 6.4 | 30 | 3.4 | 88 | 5 | 6 | 95.0 | 5.0 | 0.0 |
| C2/10 | 60 | 61.3 | 6.5 | 47 | 0.4 | 92 | 4 | 5 | 100.0 | 0.0 | 0.0 |
| C2/11 | 120 | 123.6 | 6.4 | 50.5 | 14.7 | 41 | 30 | 30 | 98.1 | 1.9 | 0.0 |
| C2/12 | 120 | 123.6 | 6.4 | 52 | 16.1 | 42 | 29 | 29 | 98.5 | 1.5 | 0.0 |
| C2/13 | 120 | 123 | 6.4 | 54 | 25.7 | 43 | 27 | 29 | 93.5 | 6.5 | 0.0 |
| C2/14 | 120 | 123 | 6.5 | 71 | 17.2 | 51 | 22 | 27 | 92.6 | 7.3 | 0.1 |
| C2/15 | 120 | 123 | 6.5 | 75 | 16.9 | 51 | 22 | 27 | 91.4 | 8.4 | 0.3 |
| C2/16 | 120 | 122.6 | 6.4 | 79 | 13.9 | 51 | 22 | 27 | 93 | 7 | 0 |
| C2/17 | 120 | 122.6 | 6.4 | 95 | 11.9 | 51 | 22 | 27 | 90 | 10 | 0 |
| C2/18 | 120 | 122.6 | 12.8 | 97 | 8.6 | 54 | 19 | 27 | 85 | 15 | 0 |
| C2/19 | 120 | 122.6 | 12.8 | 98 | 5.6 | 64 | 15 | 21 | 67 | 32 | 1 |
| C2/20 | 120 | 122.6 | 12.8 | 100 | 4.0 | 67 | 14 | 19 | 85 | 14 | 1 |
| C2/21 | 120 | 122.6 | 12.8 | 102 | 3.8 | 68 | 14 | 18 | 85 | 14 | 1 |
| | | RIG SHUTDOWN OVER WEEKEND (120° C.→Room Temp, C₂H₄ OFF/N₂ PURGE, 2500→0 MPa) AND RE-STARTED (same method as at start of run) | | | | | | | | | |
| C2/22 | 120 | 122.3 | 6.4 | 103 | 1.9 | 63 | 16 | 20 | 94 | 6 | 0 |
| C2/23 | 120 | 122.3 | 6.4 | 104 | 3.2 | 58 | 19 | 24 | 95 | 5 | 0 |
| | | RIG SHUTDOWN AS ABOVE; CATALYST REGENERATED (Room Temp→500° C./10 h/AIR→300° C./3 h/N₂→ Room Temp START-UP AS AT START OF RUN | | | | | | | | | |
| C2/24 | 20 | 28.3 | 6.4 | 105 | 27.1 | 44 | 36 | 20 | 100.0 | 0.0 | 0.0 |
| | | | | | | LIQUID (NOT COLLECTED) | | | | | |
| C2/25 | 20 | 30 | 6.4 | 106 | 90.8 | 44 | 34 | 23 | 99.1 | 0.9 | 0.0 |
| | | | | | | LIQUID (NOT COLLECTED) | | | | | |
| C2/26 | 20 | 30.6 | 6.4 | 107 | 91.5 | 50 | 29 | 21 | 98.0 | 2.0 | 0.0 |
| | | | | | | LIQ = 1.2 g/h | | | | | |

TABLE 2-continued

ETHYLENE OLIGOMERIZATION

| RUN REF | APPLIED TEMP (°C.) | CATALYST AV BED TEMP | ETHYLENE WHSV | HOS | ETHYLENE CONV (C mol %) | % SELECTIVITY TO C4's | | | % SELECTIVITY | | |
|---|---|---|---|---|---|---|---|---|---|---|---|
| | | | | | | 1-C4= | t-C4 = 2 | c-C4 = 2 | C4's | C6's | C8's |
| C2/27 | 20 | 31.3 | 6.4 | 110 | 87.5 | 57 LIQ = 0.44 g/h | 25 | 19 | 95.3 | 4.7 | 0.0 |
| C2/28 | 20 | 25.6 | 6.4 | 127 | 39.1 | 70 LIQ = 0.04 g/h | 17 | 13 | 90.7 | 8.8 | 0.5 |
| C2/29 | 20 | 24.6 | 6.4 | 130 | 33.1 | 72 | 16 | 12 | 89.8 | 9.7 | 0.5 |
| C2/30 | 20 | 23.6 | 6.4 | 134 | 29.0 | 73 | 15 | 12 | 92.4 | 7.3 | 0.2 |
| C2/31 | 20 | 22 | 6.4 | 151 | 16.3 | 80 | 11 | 9 | 96.6 | 3.4 | 0.0 |
| C2/32 | 20 | 21 | 6.4 | 154 | 15.3 | 81 | 11 | 9 | 96.7 | 3.3 | 0.0 |
| C2/33 | 20 | 21.6 | 6.4 | 157 | 15.0 | 82 | 10 | 8 | 94.2 | 5.8 | 0.0 |
| C2/34 | 20 | 20.6 | 6.4 | 223 | 0 | 0 | 0 | 0 | 0 | | |
| | RIG SHUTDOWN AS ABOVE; CATALYST REGENERATED (Room Temp→500° C./10 h/AIR→300° C./3 h/N₂→ Room Temp→START-UP AS AT START OF RUN | | | | | | | | | | |
| C2/35 | 20 | 27.3 | 6.3 | 224 | 26 | 48 | 31 | 21 | 100 | 0 | 0 |
| C2/36 | 20 | 29 | 6.3 | 225 | 86 | 56 | 26 | 19 | 96 | 4 | 0 |
| C2/37 | 20 | 29 | 6.3 | 226 | 77 | 57 | 25 | 18 | 93 | 7 | 0 |
| C2/38 | 20 | 28 | 12.5 | 227 | 22 | 68 | 19 | 13 | 94 | 6 | 0 |
| C2/39 | 20 | 26.3 | 12.5 | 228 | 19 | 76 | 14 | 11 | 96 | 4 | 0 |
| C2/40 | 20 | 28.6 | 12.5 | 229 | 16 | 80 | 11 | 9 | 96 | 4 | 0 |
| C2/41 | 20 | 27.6 | 12.5 | 230 | 12 | 85 | 8 | 7 | 89 | 11 | 0 |
| C2/42 | 20 | 24 | 12.5 | 231 | 10 | 86 | 8 | 6 | 83 | 17 | 0 |
| C2/43 | 20 | 21 | 12.4 | 246 | 1.2 | 95 | 2 | 2 | 100 | 0 | 0 |
| C2/44 | 20 | 20.3 | 12.4 | 248 | 1.0 | 96 | 2 | 2 | 100 | 0 | 0 |
| C2/45 | 20 | 20.6 | 6.2 | 250.5 | 3.0 | 93 | 3 | 3 | 100 | 0 | 0 |
| C2/46 | 20 | 20.66 | 6.2 | 251.5 | 2.8 | 93 | 3 | 3 | 97 | 3 | 0 |
| C2/47 | 30 | 30.6 | 6.2 | 253.5 | 4.2 | 91 | 4 | 5 | 97 | 3 | 0 |
| C2/48 | 30 | 30.6 | 6.3 | 270 | 1.2 | 94 | 3 | 3 | 100 | 0 | 0 |
| C2/49 | 60 | 61.6 | 6.3 | 272 | 2.4 | 88 | 6 | 7 | 95 | 5 | 0 |

TABLE 3

ETHYLENE OLIGOMERIZATION AND METATHESIS

| RUN REF | APPLIED TEMP (°C.) | CATALYST BED TEMP | C₂H₄ WHSV(1) | HOS | ETHYLENE CONV (C mol %) | % SELECTIVITY TO C4='s | |
|---|---|---|---|---|---|---|---|
| | | | | | | 1-C4= | ISO-C4= |
| C3/1 | 20 | 24.6 | 1.9 | 1 | 40 | 58.0 | 0.0 |
| C3/2 | 20 | 26.3 | 1.9 | 3 | 96 | 29.1 LIQUID = ~0.1 g/h | 2.6 |
| C3/3 | 20 | 26.3 | 1.9 | 6 | 76 | 76.4 LIQUID = 0.2 g/h | 1.2 |
| C3/4 | 20 | 30.6 | 1.9 | 23 | 34 | 95.4 | 0.9 |
| C3/5 | 20 | 25.3 | 1.9 | 27 | 30 | 96.5 | 1.0 |
| C3/6 | 20 | 24.3 | 1.9 | 31 | 27 | 97.1 | 1.1 |
| C3/7 | 20 | 23.6 | 1.9 | 47 | 16 | 97.3 | 2.0 |
| C3/8 | 20 | 22 | 1.9 | 53 | 8 | 97.7 | 2.1 |
| C3/9 | 20 | 21.3 | 1.9 | 55 | 7 | 97.4 | 2.2 |

| RUN REF | % SELECTIVITY TO C4='s | | % SELECTIVITY (C mol) | | | | | |
|---|---|---|---|---|---|---|---|---|
| | t-C4 = 2 | c-C4 = 2 | C4='s | C6='s | C8='s | C3= | C5='s | C7='s |
| C3/1 | 30.9 | 11.0 | 9.8 | 1.1 | 0.1 | 76.4 | 12.6 | 0.0 |
| C3/2 | 49.1 | 19.2 | 50.1 | 2.1 | 0.0 | 30.2 | 17.5 | 0.1 |
| C3/3 | 16.3 | 6.1 | 41.4 | 7.0 | 0.1 | 35.2 | 15.6 | 0.8 |
| C3/4 | 2.8 | 0.9 | 51.3 | 4.4 | 0.4 | 36.4 | 6.8 | 0.8 |
| C3/5 | 1.9 | 0.6 | 55.6 | 2.4 | 0.0 | 36.6 | 5.2 | 0.2 |
| C3/6 | 1.4 | 0.5 | 58.0 | 2.1 | 0.3 | 34.7 | 4.6 | 0.3 |
| C3/7 | 0.4 | 0.2 | 73.2 | 3.7 | 0.0 | 15.5 | 7.3 | 0.2 |
| C3/8 | 0.2 | 0.0 | 72.4 | 5.8 | 0.1 | 14.7 | 4.5 | 2.5 |
| C3/9 | 0.2 | 0.1 | 76.0 | 3.2 | 0.0 | 16.1 | 3.8 | 1.0 |

(1) WHSV based on both catalysts
WHSV 6.4 based on nickel catalyst

I claim:

1. A process for the conversion of ethylene to a mixture of olefins predominating in 1-olefins said process comprising
   a. feeding ethylene through a bed of an oligomerization catalyst to form an oligomer predominating in C2–C6 olefins and
   b. feeding the oligomer so formed wherein said oligomer is optionally mixed with further aliquots of ethylene so as to maintain a concentration of ethylene in the oligomer to at least 50% by volume through a catalyst bed to metathesise the oligomer feed to a mixture of olefinic products predominating in C2–C6 1-olefins.

2. A process according to claim 1 wherein the oligomerization catalyst used in step (a) comprises at least one metal or at least one oxide of a metal selected from Groups VIA, VIIA and VIIIA according to the Periodic Table (IUPAC) deposited or impregnated on a support.

3. A process according to claim 2 wherein the oligomerization catalyst used in step (a) has 0.1–50% w/w of the metal as such or in the form of its oxide based on the total weight of the catalyst and the support.

4. A process according to claim 1 wherein the oligomerization catalyst is a supported nickel oxide.

5. A process according to claim 1 wherein the support for the oligomerization catalyst is an aluminosilicate which has a silica to alumina ratio of 20:1 to 500:1.

6. A process according to claim 1 wherein the oligomerization catalyst is activated prior to use by calcining initially in air and then optionally in an inert atmosphere at an elevated temperature.

7. A process according to claim 1 wherein the oligomerization reaction is carried out at a temperature ranging from ambient to 120° C.

8. A process according to claim 1 wherein the oligomerization catalyst and the reaction conditions used are such that the conversion of ethylene to the oligomer is maintained below 30% at steady state.

9. A process according to claim 1 wherein the oligomer feed to the metathesis step (b) is such that the concentration of ethylene in this oligomer feed is at least 50% v/v, said concentration of ethylene being achieved optionally by admixing the oligomerization products with further aliquots of fresh ethylene.

10. A process according to claim 1 wherein the metathesis catalyst is a heterogeneous catalyst and comprises a metal oxide deposited or impregnated on a support.

11. A process according to claim 10 wherein the amount of metal oxide on the support in the metathesis catalyst is in the range from 0.1 to 15% w/w based on the total weight of the metal oxide and support.

12. A process according to claim 1 wherein the metathesis catalyst comprises one or more of the metal oxides selected from oxides of rhenium, tungsten, cobalt and molybdenum.

13. A process according to claim 10 wherein the heterogeneous metathesis catalyst comprises at least one support selected from alumina, phosphated alumina, silica and aluminosilicates.

14. A process according to claim 10 wherein the heterogeneous metathesis catalyst comprises rhenium heptoxide on alumina.

15. A process according to claim 1 wherein the steps of oligomerization and metathesis are carried out under the same conditions of reaction temperature and pressure.

16. A process according to claim 1 wherein the steps of oligomerization and metathesis are carried out sequentially in a single reactor.

* * * * *